United States Patent [19]

Webster et al.

[11] Patent Number: 4,987,582
[45] Date of Patent: Jan. 22, 1991

[54] X-RAY FLUORESCENCE IMAGING OF ELEMENTS

[75] Inventors: Jackie R. Webster, Irvine; Keith V. Pearson, Wilmington; David B. Chang, Tustin; Norton L. Moise, Pacific Palisades; Victor Vali, Laguna Hills, all of Calif.

[73] Assignee: Hughes Aircraft Company, Los Angeles, Calif.

[21] Appl. No.: 423,831

[22] Filed: Oct. 19, 1989

[51] Int. Cl.$^5$ .................... G21K 1/06; G01N 23/223; G01N 23/20; G01T 1/36
[52] U.S. Cl. ........................................ 378/85; 378/49; 378/70; 378/82; 378/86
[58] Field of Search ........................ 378/19, 49, 59, 70, 378/73, 76, 156, 46, 85, 82, 86, 48, 49, 84

[56] References Cited

U.S. PATENT DOCUMENTS 2,816,234 12/1957 Ellis ........................................ 378/70
3,402,292 9/1968 Baecklund ............................ 378/49
3,806,726 4/1974 Ishijima ................................. 378/49

OTHER PUBLICATIONS

Picker X-ray Corporation; "X-Ray Spectrometry"; 10/20/65.

Primary Examiner—Janice A. Howell
Assistant Examiner—Don Wong
Attorney, Agent, or Firm—Michael W. Sales; Wanda Denson-Low

[57] ABSTRACT

A system for detecting the presence of known materials in a body or container. The system incorporates a gamma or X-ray source for irradiating the body with gamma rays to produce X-ray fluorescence of materials contained therein. A directionally discriminate X-ray detector is positioned to intercept X-rays emitted from the body and is adapted to pass only those X-rays having a predetermined wavelength and incident from a specific direction that are characteristic of a material of interest contained in the body. The detector includes a dislocation free single crystal having substantially parallel input and output surfaces. A second crystal aligned parallel to the first crystal may be disposed at a position offset from the first crystal to receive the X-rays transmitted by the first crystal in order to discriminate between materials fluorescing within the body. In a specific embodiment of the invention, the first detector comprises an elongated crystal which pass X-rays in accordance with the Borrmann effect. A plurality of the crystals are arranged in a linear array and the container is either scanned with the array or the container passed linearly past the array. The detected X-rays are measured in intensity and the data is processed by suitable data processor to generate a video image indicative of the presence and shape of the specific materials for which the system is adapted. In yet another specific embodiment of the invention, a plurality of such arrays can be arranged with the input surfaces of the crystals disposed at different Bragg angles to simultaneously detect the presence of a selected group of materials.

6 Claims, 1 Drawing Sheet

X-RAY FLUORESCENCE IMAGING OF ELEMENTS

BACKGROUND

The present invention relates to systems for detecting the presence of concealed materials, and in particular to such a system which uses gamma-ray induced X-ray fluorescence and a scanning spectroscope to detect the presence of specific material in concealed locations such as luggage or other containers.

The use of X-rays to detect or examine the contents of luggage, packages and the like is well known. Such systems, however, are only capable of detecting the presence of high density elements such as steel, lead and the like. Many materials cannot be detected with current X-ray systems.

It has been proposed to use fast neutron activation of concealed materials for the detection of low density elements. It is known that some elements like nitrogen produce an isotope that emits a beta decay positron which in turn reacts with electron producing a 511 keV annihilation gamma ray. However, the resulting nucleus that produces these positrons has a half life of about ten minutes. This creates problems since even after one hour the radioactivity of the sample has dropped by only a factor of 5. Further, even using high-flux fast neutron sources, the resultant count rate of the emitted gamma rays is sufficient only to determine the presence of a particular element in a sample and not to get is spatial distribution. To produce a spatial distribution picture requires a long period of time, typically, in excess of one hour. Such systems require the use of complex technology and are expensive.

Therefore, there has been a need for a system that detects low density materials concealed in articles such as luggage and containers and the like, which is capable of producing a real-time detection of such materials and is capable of providing a spatial distribution or picture of these materials.

SUMMARY OF THE INVENTION

The invention is a system for detecting the presence of known materials in a body or container, or the like. The system incorporates a gamma or X-ray source such as an X-ray tube for irradiating the body with gamma rays to produce X-ray fluorescence of materials contained therein. A directionally discriminate X-ray detector arrangement is positioned to intercept X-rays emitted from the body and which passes only those X-rays having a predetermined wavelength characteristic of a material of interest and from a specific direction. The detector arrangement comprises a single crystal material that passes X-rays in accordance with the Borrmann effect. A typical crystal comprises single-crystal dislocation-free silicon, for example. A second crystal may be disposed in an axially offset position relative to the first crystal to receive the X-rays transmitted by the first crystal for discriminating X-rays emanating from different materials and hence remove ambiguity.

A specific embodiment of the invention, a plurality of the crystals are arranged in a linear array and the container is either scanned with the array of the container passed linearly pas the array. The detected X-rays are measured in intensity and the data is processed by suitable data processor to generate a video image indicative of the presence and shape of the specific material for which the system is adapted to detect. In yet another specific embodiment of the invention, a plurality of such arrays may be arranged with the input surfaces of the crystals disposed at different Bragg angles to simultaneously detect the presence of a selected group of materials.

It is therefore a feature of the invention to provide a system for detecting the presence of specific low density materials concealed within a container in real time. It is another feature of the invention to provide such a system for detecting gamma ray induced X-ray fluorescence of low density materials. Still another feature of the invention is to provide a system that incorporates elongated dislocation-free single crystals for selectively transmitting X-rays of predetermined wavelength to a detector, the wavelengths being characteristic of specific materials of interest. Yet another feature of the invention is to provide a system that incorporates an array of crystals arranged in a linear array and adapted to scan a container to provide a visual image indicative of the shape, size, and location of specific materials within the container in real time. Yet another feature of the invention to to provide a system that is relatively inexpensive and which can be operated without creating unnecessary radiation risks.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
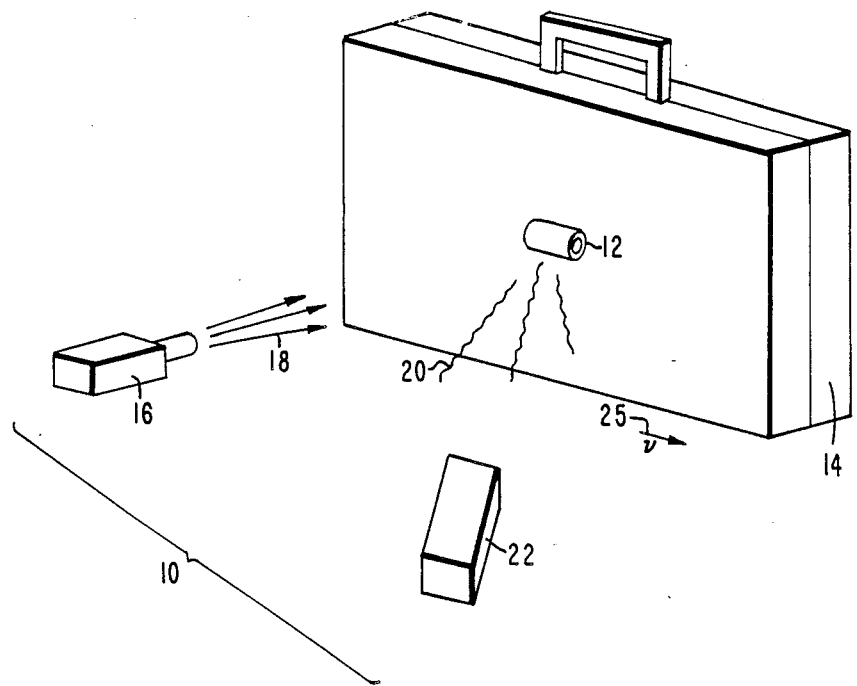
FIG. 1 is a perspective diagram of the detector system in accordance with the principles of the present invention.

Referring now to the drawings, FIG. 1 shows a system 10 in accordance with the principles of the present invention. The system is adapted to detect the presence of materials 12 concealed within a container 14 such as a suitcase, for example. The system 10 comprises a gamma ray source 16, or alternatively an X-ray source. The gamma ray source 16 may comprise an Americium 241 radioactive source, or may comprise a compact linear electronic accelerator and tungsten target, or a small compact betatron, or an X-ray tube, for example. The source 16 emits a conical beam of gamma rays indicated by arrows 18 which impinge upon and penetrate the container 14 and the materials 12 therein. As is well known, the gamma rays produce coherent scattering of X-rays by the atoms of the elements of which the container 14 and materials 12 are comprised. These X-rays result from gamma ray collisions with the K and L band electrons of the container 14 and materials 12. It is further well known that the X-rays emitted by an element have an energy or wavelength that is uniquely characteristic of the element. These X-rays, indicated by waved lines 20, will vary in wavelength or energy from relatively low energy to relatively high energy.

For example, the fluorescent X-rays from plastic explosives and drugs have relatively low energy, in the range of several keV, whereas nuclear explosives have relatively high energy, on the order of 100 keV. These X-rays are detected by an X-ray detector arrangement 22 and described at more detail below.

Figure 2:
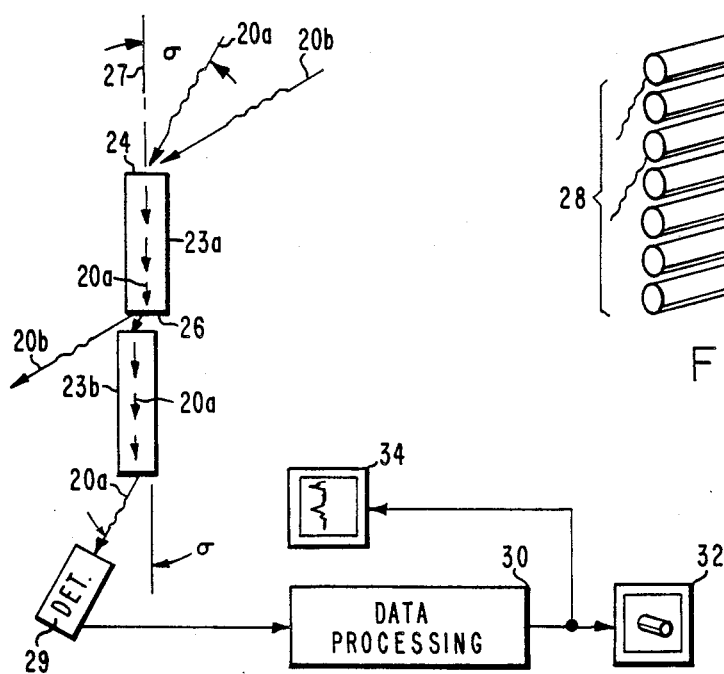
FIG. 2 is an illustration of a typical crystal and intensity detector in accordance with the invention shown in conjunction with a data processing system.

Referring now to FIG. 2, the detector arrangement 22 comprises an elongated signal dislocation-free crystal 23a made of a material such as silicon for example. In accordance with now well-known principles, X-rays incident upon the end or input surface 24 of the crystals 23a are absorbed or reflected. However, X-rays 20a, 20b of a specific wavelength incident upon input surface 24 at an angle defined as the Bragg angle will pass through the length of the crystal 23a with very little attenuation. The Bragg angle for transmission is given generally by the equation $\lambda = 2d$ since $\sigma$, where $\lambda$ is the wavelength of the X-rays, d is the lattice spacing of the crystals atoms, and $\sigma$ is the Bragg angle relative to the axis 27 of the crystal 23a. X-rays 20a, 20b having the specific wavelength incident at the bragg angle are therefore transmitted by the crystal 23a. The transmitted X-rays 20a, 20b are then emitted from an output or transmission surface 26 of the crystal 23a in two equal parts or rays, each directed at the Bragg angle with respect to transmission surface 26. The crystal 23 a functions much as the slit of a spectrometer with the slit spacing being the lattice spacing of the atoms in the crystal 23a. The transmitted X-rays 20a, 20b may be subsequently detected by a suitable X-ray detector 29 such as a scintillation counter, proportional counter, charge coupled detector array, or the like.

The crystal 23a is positioned such that its input surface 24 faces the container 12. For a specific element of interest such as a primary constituent of explosives or a drug, for example, those X-rays 20a impacting the input surface 24 at the appropriate Bragg angle produce X-rays 20a transmitted by the crystal 23a. These transmitted X-rays 20a, since they have the correct Bragg angle and wavelength, are indicative of the presence of the specific explosives or a drug located within the container 14. X-rays emitted by various elements of and in the container 14 and located at different places in the container 14 will impact the input surface 24 at different angles. Some X-rays 20b will be incident at the Bragg angle for that material 12 and these X-rays 20b will also be transmitted through the crystal 23a.

It is possible that a plurality of materials disposed in the container 14 have wavelength and Bragg angle combinations that cause X-rays 20a, 20b to impinge at the same location on the detector 29. In order to eliminate ambiguity arising from the above possible occurrence, and to discriminate between the different materials, a second crystal 23b may be disposed at an axially offset position relative to the first crystal 23. The offset spacing permits only those X-rays 20a having a selected Bragg angle to be transmitted by the second crystal 23b. Hence, the use of the second crystal 23b eliminates ambiguity.

Operation of the system can be further enhanced by providing a linear array 28 of crystals 23. If the container 14 then passes the array 28 in a direction generally perpendicular to the array 28 as indicated by arrow 25 of FIG. 1, scanning the container 14 is effected. Accumulation of data by a data processing system 30 enables generation of an image of a specific material 12 including its size, shape, and location. Alternatively the system 10 may be adapted in various ways to scan the container 14 to generate the image. This images 32 may be displayed, or recorded on a strip chart recorder 34.

Figure 3:
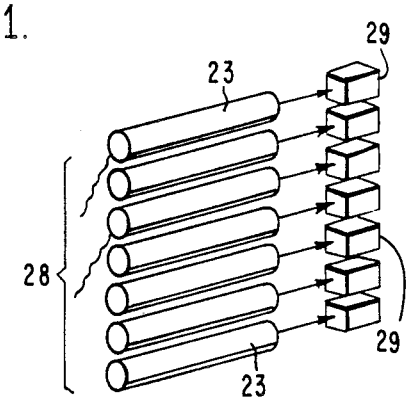
FIG. 3 is a diagram showing the arrangement of a plurality of crystals for use in scanning a container and providing a real-time image of specific materials therein.

Since it is anticipated that more than one material would be of interest when scanning an article such as luggage prior to loading aircraft or importation of packages, referring to FIG. 3, a plurality of crystals 23 may be provided in a linear array 28. In addition, each of the crystals 23 of the array are oriented at slightly different angles with respect to the container 14, in order to simultaneously detect different elements arriving at different Bragg angles. Again, well-known data processing techniques allow accumulation of this data and the generation of images showing the size, shape, and location of materials 12 within the container 14 as will as providing detection of the presence of such materials 12.

From the above description, it will now be seen that the present invention provides a unique means for detecting the presence of low density materials 12 within a container 14 by the use of gamma ray induced X-ray fluorescence. The system 10 provides a uniquely sensitive X-ray detector capable of detecting X-rays emitted by low density materials such as explosives or drugs. Orientation of the highly sensitive silicon crystal 23a and detector 29 enables the system 10 to detect a plurality of specific materials 12. The system 10 is readily adaptable for use with data processing techniques to generate images of such materials 12 within the container 14. The system 10, which can be used in conjunction with conventional X-ray scanners to detect the presence of dangerous or contraband materials, or the presence of metallic containers that are normally cannot be scanned, to precipitate careful hand searching of such articles.

Thus there has been described a new and improved system for detecting the presence of predetermined materials in a body or container. It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. A system for detecting the presence of elements in an object comprising:
    gamma ray source means for irradiating an object with gamma rays of predetermined minimum energy to produce X-ray fluorescence of elements therein;
    X-ray detector means, including a first dislocation free single crystal having substantially parallel input and transmission surfaces at opposite ends thereof, positioned to intercept X-rays radiated by said elements, and disposed at an angle of incidence with respect to the X-rays to transmit only X-rays incident at predetermined Bragg angles characteristic of a known element; and
    further including a second dislocation free single crystal disposed substantially parallel to the first crystal and having a predetermined offset therefrom to intercept and measure X-rays transmitted by the first crystal at a specific Bragg angle.

2. The system of claim 1 further including means for varying the angle of incidence of the transmission surface with respect to the second crystal and means for measuring the intensity of the X-rays radiated by material at each of a plurality of known materials.

3. The system of claim 2 further including a plurality of X-ray detector means disposed in a linear array.

4. The system of claim 3 further including means for scanning the object with the X-ray detector means including means in a direction generally perpendicular to array.

5. The system of claim 4 further including means for moving the object relative to the detector means to effect scanning of the object.

6. The system of claim 1 wherein the X-ray detector means include a dislocation free crystal having a dimension to pass X-rays of characteristic wavelength in accordance with the relationship $\lambda = 2d \sin \sigma$, where $\lambda$ is the X-ray wavelength, d is the lattice spacing of the atoms in the crystal, and $\sigma$ is the Bragg angle of the specific element of interest.

* * * * *